(12) United States Patent
Axén et al.

(10) Patent No.: US 9,757,210 B2
(45) Date of Patent: Sep. 12, 2017

(54) DENTAL IMPLANT UNIT

(71) Applicant: TIGRAN TECHNOLOGIES AB (PUBL), Malmö (SE)

(72) Inventors: Niklas Axén, Järlåsa (SE); Lars Magnus Bjursten, Malmö (SE); Sven-Erik Nilsson, Skäret (SE); Jöns Gunnar Hilborn, Sigtuna (SE)

(73) Assignee: Tigran Technologies AB (Publ), Malmö (SE)

( * ) Notice: Subject to any disclaimer, the term of this patent is extended or adjusted under 35 U.S.C. 154(b) by 0 days.

(21) Appl. No.: 14/655,866

(22) PCT Filed: Dec. 20, 2013

(86) PCT No.: PCT/SE2013/051593
§ 371 (c)(1),
(2) Date: Jun. 26, 2015

(87) PCT Pub. No.: WO2014/104966
PCT Pub. Date: Jul. 3, 2014

(65) Prior Publication Data
US 2015/0351874 A1  Dec. 10, 2015

(30) Foreign Application Priority Data
Dec. 27, 2012 (SE) .................................. 1251514-4

(51) Int. Cl.
| | |
|---|---|
| *A61C 8/00* | (2006.01) |
| *A61C 5/08* | (2006.01) |
| *A61C 8/02* | (2006.01) |
| *A61C 13/08* | (2006.01) |
| *A61K 6/00* | (2006.01) |
| *A61K 6/04* | (2006.01) |
| *A61K 33/38* | (2006.01) |
| *A61C 13/00* | (2006.01) |
| *A61L 27/06* | (2006.01) |
| *A61L 27/54* | (2006.01) |

(52) U.S. Cl.
CPC ............. *A61C 5/08* (2013.01); *A61C 8/005* (2013.01); *A61C 8/0006* (2013.01); *A61C 8/0015* (2013.01); *A61C 13/0006* (2013.01); *A61C 13/082* (2013.01); *A61K 6/0023* (2013.01); *A61K 6/04* (2013.01); *A61K 33/38* (2013.01); *A61L 27/06* (2013.01); *A61L 27/54* (2013.01); *A61L 2300/104* (2013.01); *A61L 2300/406* (2013.01); *A61L 2300/41* (2013.01); *A61L 2300/412* (2013.01); *A61L 2300/414* (2013.01); *F04C 2270/0421* (2013.01); *Y10T 29/49568* (2015.01)

(58) Field of Classification Search
CPC ....... A61C 5/08; A61C 8/0006; A61C 8/0015; A61C 8/005; A61K 6/04; A61L 27/06; Y10T 29/49568
See application file for complete search history.

(56) References Cited

U.S. PATENT DOCUMENTS

| | | | |
|---|---|---|---|
| 2006/0154206 A1* | 7/2006 | Petersson | A61C 8/0012 433/201.1 |
| 2009/0220913 A1* | 9/2009 | Geis-Gerstorfer | A61C 13/0003 433/173 |

FOREIGN PATENT DOCUMENTS

| | | |
|---|---|---|
| EP | 0702940 A2 | 3/1996 |
| WO | 9205745 A1 | 4/1992 |
| WO | 2006043166 A2 | 4/2006 |

OTHER PUBLICATIONS

International Search Report for Application No. PCT/SE2013/051593 dated Apr. 2, 2014 in 3 pages.

* cited by examiner

*Primary Examiner* — Robert N Wieland
(74) *Attorney, Agent, or Firm* — Meyertons, Hood, Kivlin, Kowert & Goetzel, P.C.

(57) ABSTRACT

A dental implant unit includes a layer of synthetically created titanium dioxide. The dental implant unit has one end for connection and a lateral surface covering the implant unit except for the end for connection. The lateral surface includes a layer of synthetically created titanium dioxide while the end for connection is free from synthetically created titanium dioxide. Also, a method produces a whitened implantable dental unit. The method includes thermal oxidation of a dental implant unit that includes titanium.

21 Claims, No Drawings

DENTAL IMPLANT UNIT

FIELD OF THE INVENTION

The present invention relates to a dental implant unit, for instance an abutment for a dental implant.

BACKGROUND OF THE INVENTION

There are different types of abutments and dental implants. Common for many dental implant systems are components like an implant unit and at least one abutment which is connectable to the implant unit by having matching surfaces, such as by one part having a screw end and the other part having a matching threaded end or surfaces allowing fixation by cement or glue. The dental implant system is then finally connected to a dental crown.

There are known existing aesthetical issues with many dental implants. As many of the parts are made of metal, like titanium, they exhibit a dark metal surface that may become directly visible in the mouth of a patient, or visible through the gingiva of a patient.

The present invention is directed to providing an improved dental component or a system thereof as a solution to the problem disclosed above, but which dental component(s) also implies an elimination of other linked possible problems. Such issues are further discussed below.

SUMMARY OF THE INVENTION

The stated purpose above is achieved by a dental implant unit, said dental implant unit comprising titanium, wherein the dental implant unit has at least one surface (end) for connection and a lateral surface covering all of the implant unit but the connecting end and wherein the lateral surface comprises a layer of synthetically created titanium dioxide and wherein at least the end for connection is free from synthetically created titanium dioxide.

It should be noted that this first embodiment of the present invention relates to a so called full-body dental implant unit, such as a screw, abutment, implant part, bridge or crown. As may be noted from below, the present invention also embodies other types of dental implant units, such as particles, grains or granules, and this is further discussed below in relation to the method of production of the dental implant units according to the present invention.

According to one specific embodiment of the full-body dental implant units according to the present invention, the dental implant unit has a first end and a second end and wherein the dental implant unit also has a lateral surface being delimited by, and extending from, the first end and the second end and around the implant unit, and wherein the lateral surface comprises a layer of synthetically created titanium dioxide and wherein at least one of the first end and the second end is free from synthetically created titanium dioxide.

A dental implant unit is a connecting element. A dental implant unit according to the present invention may be an abutment, comprising one or several abutment parts, such as screws, linkers, etc. Furthermore, a "several parts" abutment may be provided in a bridge dental system according to the present invention, or be an abutment with several connectable parts being provided for e.g. a single unit restoration. Furthermore, besides the above mentioned, a dental implant unit according to the present invention may be a implant part as such, such as a single implant or a bridge, or in fact constitute one or several crowns. All of the above may constitute a dental implant unit according to the present invention. Also combinations of these are of course embodied by the present invention.

The dental implant unit, such as an abutment, according to the present invention may be of any type existing on the market today. To mention some existing types of abutments, there are inert alia, bridge abutments, and partial denture abutments as well as prosthetic implant abutments.

Prosthetic implant dental implants and abutments known today can be made of different materials, such as metals like titanium or gold, or ceramic materials like zirconium dioxide (zirconia) or plastic materials like PEEL (polyetheretherketone). Zirconia is often used to better complement the aesthetics of a dental implant restoration. PEEK is sometimes used for provisional abutments. Prosthetic abutments are connected to the dental implants via a screw. The screw needs to be tightened securely so there is no risk for the abutment screw to loosen.

Furthermore, the expression "synthetically created titanium dioxide" implies that titanium has been oxidised to titanium dioxide of the dental implant unit according to the present invention. This implies that a chemical conversion has occurred. Moreover, this also implies that methods like sputtering or spraying, or other such coating techniques, where additional titanium oxide material is applied to a surface, are not contemplated according to the present invention in relation to the feature of incorporating a titanium dioxide layer.

According to the present invention there is provided a dental implant unit which exhibits superior aesthetics as wells as mechanical benefits, when being compared to existing alternatives today. As said above, zirconium ceramics are used today as a material for providing whitish dental implants and abutments. Zirconium ceramics have proven to have disadvantages in terms of exhibiting a chemical phase transformation, which is undesirable for a dental implant.

Furthermore, another technique used today is spray coating with white colour on implants and abutments which e.g. have a metal dark surface. The problems with this technique are the degradation and abrasion of such coatings. As the surface loosens its white appearance, the patient has to obtain new white coatings from time to time.

As said above, the present invention is directed to all kinds of implants and implant parts, such as abutments, which are visible in the mouth of a patient, e.g. also through the gingiva.

According to one specific embodiment of the present invention, the dental implant unit is an abutment. As mentioned above, the abutment may be one piece or consist of several pieces, connectable to each other or connectable to different parts of e.g. a bridge. According to one specific embodiment of the present invention, the dental implant unit is an abutment and the abutment has an implant connecting end and a crown connecting end, wherein the abutment also has a lateral surface being delimited by, and extending from, the implant connecting end to the crown connecting end and around the abutment, and wherein the lateral surface comprises a layer of synthetically created titanium dioxide and wherein the implant connecting end is free from synthetically created titanium dioxide. In relation to what has been disclosed above, it is important to understand that the expression "an implant connecting end" of the abutment implies that end facing towards the implant when being connected, however a connecting screw or so may be positioned in between that end of the abutment and the actual implant piece. The same is also valid for the crown connecting end, although normally the abutment is directly connected to the crown. Only for clarification reasons, possible synonyms for the first end and second end or implant connecting end and the crown connecting end may e.g. be a proximal end and a distal end, respectively.

Furthermore, it should be noted that some implant constructions are not attached via continuous screw units, but are linked by other means. One such example is abutments where the crowns are glued in place. Also in this case, the dental implant units, such as an abutment, or an implant, etc., according to the present invention find use. Furthermore, also for an abutment such as above, it is evident that only the implant connecting end has to be free from synthetically created titanium dioxide, as this part is the only end where there will be a mechanical locking. The other end must only allow a crown to be attached by use of a suitable glue.

According to another specific embodiment, the dental implant unit is an abutment comprising more than one piece, and wherein all connectable ends are free from synthetically created titanium dioxide.

According to yet another specific embodiment of the present invention, the dental implant unit is an implant and at least part of the lateral surface comprises a layer of synthetically created titanium dioxide. The part of the implant important to comprise a layer of synthetically created titanium dioxide is that part being visible or in risk of being visible, such as through the gingiva. The entire lateral surface may also comprise a layer of synthetically created titanium dioxide, as disclosed below, however at least the end connectable to an abutment is free from synthetically created titanium dioxide in the connectable parts.

According to yet another specific embodiment of the present invention, the dental implant unit is a crown. The entire crown suitably has a layer of synthetically created titanium dioxide, i.e. besides that part of an end which is connectable to an abutment.

According to yet another specific embodiment of the present invention, the dental implant unit is a bridge. The entire bridge suitably has a layer of synthetically created titanium dioxide, i.e. besides that part of surfaces that are connectable to an abutment or artificial teeth.

According to the present invention, the whitish colour is obtained by a superior material form which has both advantages in terms of mechanical resistance as well as the provision of anti-inflammatory properties. It should be noted from above, that the expression "synthetically created" implies that the titanium dioxide is at least not only a naturally occurring titanium dioxide. Such natural titanium dioxide exists on a titanium surface in small amounts when the titanium metal is contacted with air. When titanium is exposed to air or water, an oxide layer is spontaneously formed. This spontaneously formed oxide layer is 4-10 nm thick and consists predominantly of $TiO_2$, Ti(IV), with smaller amounts of Ti(III) and Ti(II) present in the oxide. Such natural surfaces are, however, not whitish as such, as the amounts of oxide are very small. According to the present invention, however, there is provided a "synthetically created" titanium dioxide in an amount so the surface is whitened.

Furthermore, it should also be understood that although the original material of the dental implant unit according to the present invention is titanium, also other materials, such as other metals, or trace amounts of impurities, may exist. For instance, the implant may have other metal contents, so the base material may in fact be a titanium alloy. A pure titanium "core" with an existing synthetically created titanium dioxide outside in/on the surface is of course a highly interesting embodiment of the present invention. Furthermore, it is of interest to provide an implant unit, e.g. a crown or abutment, which is whitish in all important parts of the lateral surface, however the thickness of the provided titanium dioxide may vary. Moreover, if parts of the lateral surface of the implant are not important to whiten, such parts do not have to comprise an oxide layer.

As noted from above, at least one end, like the implant connecting end is free from synthetically created titanium dioxide. This feature according to the present invention is also of great importance. As the implant connecting end of e.g. an abutment comprises some kind of connecting unit, like a threaded cavity or a screw portion, this part shall not be oxidised. This is not suitable in terms of material properties for such connectable parts. Example of such properties are dimension accuracy and that the surface is smooth enough to allow for screwing together threaded parts. Those parts should thus still consist of metal in the surface, as they are intended to be connected by e.g. a "screw and thread" connection. This is valid irrespectively if the dental implant unit is a screw, an entire abutment, only a linker of an abutment, an implant part or a bridge, etc.

Moreover, titanium dioxide has several advantages. As said, the oxide has a whitish colour which is advantageous for aesthetic reasons in dental applications. Moreover, titanium dioxide has good mechanical properties, being brittle and not tough in comparison to titanium metal, and therefore easy to cut and shape. However, titanium dioxide does not sustain such high stresses which titanium metal may bear. Moreover, titanium dioxide has also been shown to have anti-inflammatory and bone generating properties.

There are no titanium dioxide white dental implant units, such as abutments, on the market today, especially none having "protected" connectable ends which are of metal. It should, however, be mentioned that there exists implants which to some extent also may incorporate titanium oxide. For instance in WO2008/128756 there is disclosed a dental implant, which implant can comprise a body, attachment means for attaching the implant to bone, and a recess. The outer surface of the implant may be provided with a surface treated to enhance tissue growth, and the treated surface may comprise a crystalline and phosphate enriched titanium oxide microstructured surface, with open pores in the low micrometer range. As should be understood, the surface of the implant according to WO2008/128756 is not oxidised and made whitish. Furthermore, the actual surface coating is in fact phosphate enriched titanium oxide which is porous to allow for an enhanced tissue growth.

Moreover, in JP2007098054 there is disclosed a dental implant and abutment, which abutment has a coating containing titanium oxide powder covered by hydroxy apatite or hydroxy apatite fluoride. The coating is said to be provided to control the accumulation of dental plaque. Also in this case, there is not provided an abutment having a synthetically created titanium dioxide outermost layer implying a white lateral surface, such as according to the present invention. Moreover, there is no hint of protecting end parts such as according to the present invention.

There are also other known methods for modifying dental implants and associating parts like abutments and so, such as acid etching, e.g. with oxalic acid. Such methods may be used also to whiten the surface of e.g. titanium. Another known surface treatment which is used today only to modify is blasting. However, there is no method disclosed where there is made an actual full oxidation of the titanium surface to create synthetic titanium dioxide, particularly not when also making sure to protect parts which should not be oxidized, such as according to the present invention.

Furthermore, it may also be said that there are other existing products, also dental products, which comprises a titanium dioxide white surface. For instance, in WO2009/154560 there is disclosed a porous titanium dioxide block, for implantation in the maxillofacial area of a human or animal, wherein the porous block is made of titanium dioxide, has a porosity of at least 60%; and is a geometrical structure shaped to fit at least a part of a degraded alveolar process of the human or animal. As understood from above, the product described in WO2009/154560 is not a dental implant unit, like an abutment or a crown. Furthermore, the intention of WO2009/154560 is to provide a block being porous at intended portions for inducing bone ingrowth and where other non-bone contacting surfaces are non-porous to counteract tissue ingrowth.

Moreover, in WO2008/103081 there is described an implant with anti-inflammatory or antibacterial effects, or both, the implant being intended for implantation in a human or an animal body, the implant comprising at least one porous grain or granule, where the at least one porous grain or granule comprises titanium, one or more titanium oxides or titanium alloy and has a titanium oxide layer on its surface; has a mean length from one side to the opposite side, through a geometrical centre, of up to 5 mm, and has a mean specific surface area of at least 0.15 $m^2$/g according to the BET method. According to WO2008/103081, the expression "implant" implies the form of a single piece body, including one grain or granule or an agglomerate of particles and/or grains, bonded together or not. According to one specific embodiment of the invention disclosed in WO2008/103081, the implant has a titanium oxide layer on its surface with a substantial thickness of at least 500 nm and is yellowish and/or whitish.

Also other dental related products are disclosed with the possibility of having a titanium oxide layer. For instance, in WO2010/097214 there is disclosed a position locator for indicating the position and orientation of a dental implant. The position locator is made of an optically opaque material, such as titanium, and has an outer surface detectable by an optical scanner, e.g. with a layer of porous titanium oxide applied through anodic oxidation.

Also in the case of both WO2008/103081 and WO2010/097214 it is evident that neither of them is related to a dental implant unit, e.g. an abutment, such as according to the present invention. Moreover, the protective feature of the present invention is not revealed or hinted in either of these documents.

ADDITIONAL SPECIFIC EMBODIMENTS OF THE INVENTION

Different aspects and specific embodiments of the present invention are disclosed below.

According to one specific embodiment of the present invention, the entire lateral surface contains a layer of synthetically created titanium dioxide. As mentioned before, the thickness of the layer may vary over the lateral surface. Moreover, it is according to the present invention also possible with a surface where some portions, such as for instance peripheral portions, are not covered by titanium dioxide. The important thing is that surfaces which are visible, also e.g. through the gingival, comprise titanium dioxide and are as such whitish. According to the specific embodiment above, the entire lateral surface may be white or whitish. According to another specific embodiment of the present invention, all parts of the lateral surface being visible when being used in the mouth of a patient, i.e. also through the gingiva, are white or whitish.

According to yet another specific embodiment of the present invention, the layer of synthetically created titanium dioxide has a thickness of above 400 nm. The thickness may be in the range of e.g. from 400 nm, such as from e.g. 500 nm and e.g. up to 700 nm or e.g. up to 1 mm or even thicker. The thickness is of course of interest in relation to ensuring a whitish appearance, and while visible light has a wavelength of 400-700 nm, a thickness of at least 500 nm is of special interest to ensure a whitish appearance. It is, however, still interesting to keep the chemical properties of the titanium or titanium alloy to the implant while still keeping the yellowish and/or whitish appearance.

As mentioned above, at least one end, such as a first or a second end, e.g. an implant connecting end in the case of an abutment, is free from synthetically created titanium dioxide. Suitably, such connectable end is of titanium, just as the core of the dental implant unit. According to yet another specific embodiment of the present invention, both the first end and the second end are free from synthetically created titanium dioxide. When that connecting end also has connectable parts, such as being threaded for the purpose of e.g. a crown plus screw to be attachable, also here, metal properties are preferable.

Besides the whitish appearance, the dental implant unit according to the present invention also exhibits anti-inflammatory and/or antibacterial properties which are linked to the titanium dioxide surface. These properties may of course be of interest to prevent infectious diseases or bacterial attacks of the surrounding tissue in close contact with an implant system. Titanium has been reported to reduce inflammation and also to be less susceptible to infections than other materials. There are also existing reports describing unique properties of titanium due to its chemical interactions with reactive oxygen species (ROS). The catalytic property of titanium has been shown to be related to the titanium oxide on the surface being present on surfaces composed of only titanium oxide. The beneficial properties of titanium seem to be linked to its chemical interaction with a living tissue environment.

According to the present invention, such anti-inflammatory and/or antibacterial properties or other possible added properties may be enhanced, e.g. by use of additives. Therefore, according to one specific embodiment of the present invention, the lateral surface also comprises or is complemented with at least one additive.

According to one specific embodiment, the additive is silver. The bacteriostatic and fungistatic effect of silver is well known, and silver may therefore constitute a suitable additive choice for certain applications. According to yet another specific embodiment, said at least one additive is bone morphogenic factor, andronate, alfa-keto glutarate, simvastatin, gentamicin, phosphonate molecules or synthetic type I collagen, at least one active enamel substance, or a combination thereof. The use of additional antibiotics to incorporate on the surface may be an added security for the prevention of bacterial attacks. In relation to the possibility of an enamel substance, it may be mentioned that such substance may e.g. be enamel matrix, enamel matrix derivatives or enamel matrix proteins or combinations thereof, e.g. possibly also admixed with propylene glycole alginate (PGA). Combinations of different additives are also possible.

The present invention is also directed to a dental implant kit comprising a dental implant unit being an implant, an abutment or a crown, or a combination thereof. Furthermore, the implant kit may also comprise other needed units, like complementary screws and attachments units, etc. It should be noted that a dental implant kit according to the present invention may comprise an implant, an abutment or a crown according to the invention together with one or several conventional implant units, such as screws, implant parts etc. which are not oxidised or in fact even not of titanium. As an example, a dental implant kit according to the present invention may comprise an oxidised titanium abutment according to above, and a conventional titanium implant and any type of crown.

According to one specific embodiment, the kit also comprises at least one additive, such as an additive chosen from the group consisting of silver, bone morphogenic factor, andronate, alfa-keto glutarate, simvastatin, gentamicin, phosphonate(s) or synthetic type I collagen, at least one active enamel substance, or a combination thereof. Possible additives besides the ones disclosed above are e.g. fluid vehicles, such as NaCl (aq), hyaluronic acid, PEG, propylene glycole alginate (PGA), titanium peroxy gel, methyl cellulose, carbomethyl cellulose, dextran, high viscous polymeric gels, protein solutions, or a combination thereof. For instance a gel having a melting temperature above ambient temperature and below 37° C. (body temperature), possibly also comprising other additives such as according to above, is a possible additive to incorporate in a dental implant kit according to the present invention.

The present invention also relates to a method of production of a dental implant unit. According to one embodiment of the present invention there is disclosed a method for the production of a whitened implantable dental unit, said method comprising thermal oxidation of a dental implant unit comprising titanium and which may be solid or porous in the presence of fluoride ions, for the production of a whitened implantable dental unit having a surface comprising synthetically created titanium dioxide.

The thermal oxidation is performed of at least one part of the surface, however suitably on a substantial coverage of the entire surface, e.g. at least on all parts of the surface which may be visible after implantation. Moreover, the thermal oxidation does not have to be complete through the entire dental implant unit. Fact is that for full-body dental implant units according to the present invention, such as screws, abutments, implant parts, bridges or crowns, the oxidation may be performed so that only the surface becomes whitened, which implies that the oxidation is only made into a part of the body and not the entire way through. Therefore, both a full oxidation and a non-full oxidation are possible according to the present invention. As mentioned above, the dental implant unit according to the present invention may also be in the shape of particles, grains or granules, both porous and non-porous. Also in these cases both the full oxidation and partly oxidation are possible. This is further discussed below.

The method according to the present invention has several advantages. As fluoride ions are present in some form and acts as a catalyst for the oxidation, the oxidation may be formed at a lower temperature. Therefore, according to one embodiment of the present invention, the oxidation is performed in a temperature below 800° C., such as below 700° C. or even below 600° C.

A second advantage of the fluoride ions being present and getting in contact with surface of the dental implant unit is the increased bone growth and ingrowth promoting effect rendered by the fluoride. To adhere fluoride on implants has been made in the past, such as by wet chemical methods, however not via oxidation as according to the present invention.

It may further be said that according to one specific embodiment of the present invention, the fluoride ions are brought into contact with the surface of the dental implant unit before the oxidation. This may be performed by using a carrier for the fluoride ions. The fluoride ions may be available as a fluoride salt, such as sodium fluoride, in solid state form or as a solute. One example is cross linked epoxy systems, such as epoxylated polypropylene oxide/polypropylene glycol (see further discussion below).

According to the present invention the fluorinating agent can be dispersed in a liquid polymer material to allow coating of the implant unit surface. The polymer can either be a lower molecular weight precursor or a polymer liquefied by the use of a solvent which upon coating evaporates. The polymer coated screw or other implant unit containing the fluorinating agent is then heated in an oven, preferentially in the presence of air. This carrier for the fluorinating agent which is a fluorine containing compound, e.g. NaF, needs to fulfil requirements of:

1) Formation of a coating containing the above mentioned components;
2) Formation of a coating that does not liquefy to drip off the object upon heating;
3) Undergo clean thermal decomposition in the presence of air at elevated temperature without formation of char;
4) Leaving no residues that can cause discoloration, toxicity except the fluorine containing agent;

The preferred polymer fulfilling these requirements is poly(propylene oxide) that is known to decompose cleanly at temperatures between 200-300° C. without char formation. The polymer must, however, be able to form a coating that stays on the surface of the implant unit to hold the components until it is thermally decomposed. Methods to accomplish this includes the use of $\alpha$-, $\Omega$-functionalized poly(propylene oxide)s. Typical examples include polymerizable end-groups and two (or more) component condensation type systems. Preferred are systems that have a latency in cross linking.

Yet another advantage of the present invention is the decreased obtained crystallinity of the titanium dioxide produced during the oxidation, which is made possible by the decreased temperature used. The decreased crystallinity gives enhanced mechanical stability and thus, the bodies produced are easier to shape and work with in a subsequent step.

Furthermore, one advantage of the decreased temperature used is the possibility of oxidation of a full-body implant comprising both implant part (perhaps plus abutment) and also a crown being made of porcelain. Using standard oxidation temperatures in such cases renders high risk of creating blackened parts or at least a blackened strip on the porcelain crown. This is of course not optimal for aesthetic reasons.

As may be understood from the discussion above, the present invention is also directed to a whitened implantable dental unit possible to produce by the method according to the present invention. Therefore, according to one embodiment there is disclosed a whitened implantable dental unit, said dental unit comprising titanium in the form of a titanium metal or titanium alloy, and/or in the form of titanium oxide, said dental unit having a surface comprising synthetically created titanium dioxide and which surface also comprises fluoride bound to the surface. As mentioned above, both full-body implants, such as screws, abutments, implant parts, bridges or crowns, and smaller implant bodies, such as particles, grains or granules, are embodied by the present invention. Furthermore, the whitened implantable dental unit may be full oxidised or with a titanium or titanium alloy core having a titanium dioxide surface. According to one specific embodiment, the oxidation is only made on the surface. I that case the core comprises titanium, either in the form of metal or alloy. According to yet another specific embodiment, the implantable dental unit is a full-body implant and wherein the core of the implantable dental unit comprises titanium. Also in case of smaller bodies such as particles, grains or granules, these may be fully-oxidised or not. Therefore, according to one specific embodiment the implantable dental unit is a particle, grain or granule and wherein the particle, grain or granule comprises metallic titanium, in the form of metal or alloy. The metallic titanium may be located in the core of the particle, grain or granule, and where the particle, grain or granule then has a titanium dioxide layer in the surface. This is not possible when standard oxidation with high temperature is performed as it in such case is not possible to control the oxidation of such small bodies. The particle, grain or granule may of course also be fully-oxidised according to the present invention. It may further be said that the particles may typically be of micrometer size. The grains or granules may be up to 1 millimeter in size, typically from 200 micrometer up to 1 millimeter. Moreover, the grains or granules may be porous or not.

Furthermore, according to another embodiment of the present invention, a customized dental implant unit consisting of titanium at least on its surface is oxidised in a temperature above 300° C. in an environment where at least one of the first end and the second end is protected from oxidation by a protective gas or by a protective coating. The protective coating may e.g. be a paste. According to one specific embodiment in relation to this method, both ends are protected from oxidation by a protective gas or by a protective coating.

The actual protection of the titanium metal during oxidation may be performed by the use of applied layers to that or those end parts being protected. Such layers may e.g. comprise ceramic glaze raw materials, such as materials including silica. One possible example is water glass (sodium silicate). This material may be applied on the metal as a crystal water gel. The water part is removed during the heat treatment, but a protecting film of sodium silicate remains. Other paste examples are such including water glass and additives to regulate consistency, strength and resistance.

According to yet another specific embodiment of the present invention, there is provided a method for the production of dental implant unit, such as for instance one or more abutments, wherein a cylinder consisting of titanium at least on its surface is firstly oxidised in a temperature above 300° C., then secondly the finished oxidised cylinder is cut into dental implant units of which the ends are shaped.

According to the present invention, it is possible to perform the oxidation in different ways. Using a comparatively low temperature, such as 300° C.-600° C. implies that the oxidation will occur slower. To decrease the time needed it is, besides increasing the temperature, possible to increase the oxygen level. Although this accelerates the oxidation reaction, it may also give an uncontrolled oxidation. In other words, a higher temperature and controlled oxygen level are preferred for the oxidation to keep the oxidation time within a reasonable limit and have a reaction which is controllable and not dangerous. According to another specific embodiment, the oxidation is performed in a temperature of at least 800° C.

Once again it should be noted that the method according to the present invention involves an oxidation in relation to creating a layer of synthetic titanium dioxide. This oxidation converts surface titanium material to titanium dioxide by addition of oxygen at elevated temperatures. After the addition of oxygen, the metal holding "dissolved" oxygen is recrystallized to titanium dioxide crystalline form. As mentioned, techniques for adding titanium dioxide particles to a surface are not contemplated. Such coating techniques may, however, be of interest for the application of possible additives, such as silver, antibiotics etc., to the lateral surface according to the present invention.

As may be understood from above, and also relevant when discussing the oxidation conditions, there are different forms of titanium oxides. The normally mentioned titanium oxide forms are titanium(II) oxide (titanium monoxide, TiO), which is a non-stoichiometric oxide, titanium(III) oxide (dititanium trioxide, $Ti_2O_3$), trititanium pentaoxide ($Ti_3O_5$) and titanium(IV) oxide (titanium dioxide, $TiO_2$). However, there exists also other oxides, such as a composition between $TiO_2$ and $Ti_3O_5$, and they have the general formula $Ti_nO_{2n-1}$ where n ranges from 4-9. Worth mentioning, titanium(II) oxide (TiO) can be prepared from titanium dioxide and titanium metal at a temperature of 1500° C. and titanium(III) oxide can be prepared by reacting titanium dioxide with titanium metal at a temperature of 1600° C. However, titanium(IV) oxide or titanium dioxide, which is the oxide form desirable according to the present invention, is the naturally occurring oxide of titanium. This titanium dioxide occurs in nature as the naturally occurring rutile, anatase and brookite, of which rutile is the most stable form. It has previously been found that the crystalline isoforms, anatase and rutile, of titanium oxide are more efficient than the amorphous titanium oxide in the catalytic reactions, as the source of the anti-inflammatory and bactericidal properties of titanium. Therefore, according to one specific embodiment of the present invention, the titanium dioxide of the lateral surface is provided predominantly in a crystalline isoform, like anatase and rutile, or a combination thereof.

The invention claimed is:

1. Dental implant unit, said dental implant unit having a core comprising titanium, wherein the dental implant unit has at least one surface (end) for connection and a lateral surface covering all of the implant unit except the connecting end and wherein the lateral surface comprises a layer of synthetically created titanium dioxide and wherein at least the end for connection is free from synthetically created titanium dioxide, and wherein the layer of synthetically created titanium dioxide has a thickness of above 400 nm.

2. Dental implant unit according to claim 1, said dental implant unit comprising titanium, wherein the dental implant unit has a first end and a second end and wherein the dental implant unit also has a lateral surface being delimited by, and extending from, the first end and the second end and around the implant unit, and wherein the lateral surface comprises a layer of synthetically created titanium dioxide and wherein at least one of the first end and the second end is free from synthetically created titanium dioxide.

3. Dental implant unit according to claim 1, wherein the dental implant unit is an abutment.

4. Dental implant unit according to claim 1, wherein the dental implant unit is an abutment and wherein the abutment has an implant connecting end and a crown connecting end, wherein the abutment also has a lateral surface being delimited by, and extending from, the implant connecting end to the crown connecting end and around the abutment, and wherein the lateral surface comprises a layer of synthetically created titanium dioxide and wherein the implant connecting end is free from synthetically created titanium dioxide.

5. Dental implant unit according to claim 1, wherein the dental implant unit is an abutment comprising more than one piece, and wherein all connectable ends are free from synthetically created titanium dioxide.

6. Dental implant unit according to claim 1, wherein the dental implant unit is an implant, and wherein at least part of the lateral surface comprises a layer of synthetically created titanium dioxide.

7. Dental implant unit according to claim 1, wherein the dental implant unit is a crown.

8. Dental implant unit according to claim 1, wherein the entire lateral surface contains a layer of synthetically created titanium dioxide.

9. Dental implant unit according to claim 1, wherein the lateral surface is whitish.

10. Dental implant unit according to claim 1, wherein both the first end and the second end are free from synthetically created titanium dioxide.

11. Dental implant unit according to claim 1, wherein the lateral surface also comprises at least one additive.

12. Dental implant unit according to claim 11, wherein said at least one additive is silver.

13. Dental implant unit according to claim 11, wherein said at least one additive is bone morphogenic factor, andronate, alfa-keto glutarate, simvastatin, gentamicin, phosphonate(s) or synthetic type I collagen, at least one active enamel substance, or a combination thereof.

14. Method for the production of a whitened implantable dental unit, said method comprising thermal oxidation of a dental implant unit comprising titanium and being solid or porous in the presence of fluoride ions, for the production of a whitened implantable dental unit having a surface comprising synthetically created titanium dioxide.

15. Method according to claim 14, wherein the oxidation is performed in a temperature below 800° C.

16. Method according to claim 14, wherein the fluoride ions are brought into contact with the surface of the dental implant unit before the oxidation.

17. Method according to claim 16, wherein the fluoride ions are brought into contact with the surface of the dental implant unit before the oxidation by using a carrier for the fluoride ions.

18. Whitened implantable dental unit, said dental unit having a core comprising titanium in the form of a titanium metal or titanium alloy, and/or in the form of titanium oxide said dental unit having a surface comprising synthetically created titanium dioxide and which surface also comprises fluoride bound to the surface, and wherein the implantable dental unit is a particle, grain or granule.

19. Whitened implantable dental unit according to claim 18, wherein the implantable dental unit is a full-body implant and wherein the core of the implantable dental unit comprises titanium.

20. Whitened implantable dental unit according to claim 18, wherein the implantable dental unit is a particle, grain or granule and wherein the implantable dental unit comprises metallic titanium.

21. Whitened implantable dental unit according to claim 18, wherein the particle, grain or granule is fully-oxidised.

* * * * *